United States Patent
Böhm et al.

(10) Patent No.: US 10,029,263 B2
(45) Date of Patent: Jul. 24, 2018

(54) METHOD AND APPARATUS FOR SORTING PARTICLES

(71) Applicant: CYTONOME/ST, LLC, Boston, MA (US)

(72) Inventors: Sebastian Böhm, Inverness (GB); John R. Gilbert, Brookline, MA (US); Manish Deshpande, Canton, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 0 days.

(21) Appl. No.: 13/849,365

(22) Filed: Mar. 22, 2013

(65) Prior Publication Data

US 2013/0313170 A1    Nov. 28, 2013

Related U.S. Application Data

(60) Continuation of application No. 13/158,960, filed on Jun. 13, 2011, now Pat. No. 8,408,399, which is a
(Continued)

(51) Int. Cl.
*B07C 5/34* (2006.01)
*B03B 5/00* (2006.01)
(Continued)

(52) U.S. Cl.
CPC .................. *B03B 5/00* (2013.01); *B07C 5/34* (2013.01); *F15C 5/00* (2013.01); *F16K 99/0001* (2013.01);
(Continued)

(58) Field of Classification Search
CPC ... B07C 5/34; F16K 99/0046; F16K 99/0048; F16K 99/0061; F16K 99/0084;
(Continued)

(56) References Cited

U.S. PATENT DOCUMENTS 2,015,522 A    9/1935    Hoffman
2,646,882 A    7/1953    Frost
(Continued)

FOREIGN PATENT DOCUMENTS

EP    0 177 718 A2    4/1986
EP    0 745 682 A1    12/1996
(Continued)

OTHER PUBLICATIONS

Office Action issued in Canadian Application No. 2,482,869, dated Jul. 26, 2012.
(Continued)

*Primary Examiner* — Joseph C Rodriguez
(74) *Attorney, Agent, or Firm* — McCarter & English, LLP; David R. Burns

(57) ABSTRACT

A method and apparatus for sorting particles moving through a closed channel system of capillary size comprises a bubble valve for selectively generating a pressure pulse to separate a particle having a predetermined characteristic from a stream of particles. The particle sorting system may further include a buffer for absorbing the pressure pulse. The particle sorting system may include a plurality of closely coupled sorting modules which are combined to further increase the sorting rate. The particle sorting system may comprise a multi-stage sorting device for serially sorting streams of particles, in order to decrease the error rate.

21 Claims, 5 Drawing Sheets

Related U.S. Application Data continuation of application No. 12/537,802, filed on Aug. 7, 2009, now Pat. No. 7,963,399, which is a continuation of application No. 11/499,953, filed on Aug. 7, 2006, now Pat. No. 7,584,857, which is a continuation of application No. 10/940,143, filed on Sep. 13, 2004, now Pat. No. 7,104,405, which is a division of application No. 10/179,488, filed on Jun. 24, 2002, now Pat. No. 6,808,075.

(60) Provisional application No. 60/373,256, filed on Apr. 17, 2002.

(51) Int. Cl.
    *F15C 5/00* (2006.01)
    *F16K 99/00* (2006.01)
    *G01N 15/14* (2006.01)
    *B01L 3/00* (2006.01)

(52) U.S. Cl.
    CPC ...... *F16K 99/0028* (2013.01); *F16K 99/0046* (2013.01); *F16K 99/0048* (2013.01); *F16K 99/0061* (2013.01); *G01N 15/14* (2013.01); *B01L 3/5027* (2013.01); *F16K 2099/0084* (2013.01); *G01N 2015/149* (2013.01); *Y10S 209/906* (2013.01); *Y10S 209/932* (2013.01)

(58) Field of Classification Search
    CPC ...... G01N 2015/1081; G01N 2015/149; B01L 3/5027; B01L 3/502761; B01L 3/50273; B01L 3/502753
    USPC ......... 209/155, 552, 576, 906; 422/502–504, 422/507, 509, 513
    See application file for complete search history.

(56) References Cited

U.S. PATENT DOCUMENTS

| | | |
|---|---|---|
| 2,787,453 A | 4/1957 | Hibshman et al. |
| 2,850,940 A | 9/1958 | Opperman |
| 2,923,410 A | 2/1960 | Florian |
| 3,289,687 A * | 12/1966 | Dunaway ................ 137/831 |
| 3,362,421 A * | 1/1968 | Schaffer ................ F15C 1/04 137/828 |
| 3,370,538 A | 2/1968 | Hines et al. |
| 3,495,253 A | 2/1970 | Richards |
| 3,506,654 A | 4/1970 | Fried |
| 3,508,654 A | 4/1970 | Glaettli |
| 3,508,655 A * | 4/1970 | Kamentsky ................ 210/85 |
| 3,560,754 A | 2/1971 | Kamentsky |
| 3,785,390 A * | 1/1974 | Taylor ................ F15C 1/14 137/13 |
| 3,791,517 A | 2/1974 | Friedman |
| 3,827,555 A | 8/1974 | Kamentsky et al. |
| 3,906,415 A | 9/1975 | Baker |
| 3,984,307 A | 10/1976 | Kamentsky et al. |
| 3,984,621 A | 10/1976 | Propst |
| 4,050,851 A | 9/1977 | Haavik |
| 4,147,621 A | 4/1979 | Giddings |
| 4,153,855 A | 5/1979 | Feingold |
| 4,175,662 A * | 11/1979 | Zold ................ 209/552 |
| 4,284,499 A | 8/1981 | Moudgil et al. |
| 4,318,483 A | 3/1982 | Lombardo et al. |
| 4,344,844 A | 8/1982 | Townley |
| 4,361,400 A | 11/1982 | Gray et al. |
| 4,365,719 A | 12/1982 | Kelly |
| 4,426,451 A | 1/1984 | Columbus |
| 4,445,696 A | 5/1984 | Raj et al. |
| 4,526,276 A | 7/1985 | Shoor et al. |
| 4,554,427 A | 11/1985 | Flick et al. |
| 4,572,664 A | 2/1986 | Hanson |
| 4,579,173 A | 4/1986 | Rosensweig et al. |
| 4,581,624 A | 4/1986 | O'Connor |
| 4,636,149 A | 1/1987 | Brown |
| 4,676,274 A | 6/1987 | Brown |
| 4,756,427 A * | 7/1988 | Gohde et al. ................ 209/3.1 |
| 4,808,079 A | 2/1989 | Crowley et al. |
| 4,863,588 A | 9/1989 | Herron |
| 4,908,112 A | 3/1990 | Pace |
| 4,936,465 A * | 6/1990 | Zold ................ 209/3.1 |
| 4,939,081 A | 7/1990 | Figdor et al. |
| 4,963,498 A | 10/1990 | Hillman et al. |
| 5,005,639 A | 4/1991 | Leland |
| 5,030,002 A | 7/1991 | North, Jr. |
| 5,065,978 A | 11/1991 | Albarda et al. |
| 5,092,972 A | 3/1992 | Ghowsi |
| 5,101,978 A * | 4/1992 | Marcus ................ B07C 5/342 209/3.1 |
| 5,193,688 A | 3/1993 | Giddings |
| 5,265,327 A | 11/1993 | Faris et al. |
| 5,271,724 A | 12/1993 | van Lintel |
| 5,275,787 A | 1/1994 | Yuguchi et al. |
| 5,277,556 A | 1/1994 | van Lintel |
| 5,395,588 A | 3/1995 | North, Jr. et al. |
| 5,486,335 A | 1/1996 | Wilding et al. |
| 5,498,392 A | 3/1996 | Wilding et al. |
| 5,617,955 A | 4/1997 | Tanner |
| 5,632,935 A | 5/1997 | Yeoman et al. |
| 5,637,496 A | 6/1997 | Thaler et al. |
| 5,699,157 A | 12/1997 | Parce |
| 5,726,026 A | 3/1998 | Wilding et al. |
| 5,726,404 A | 3/1998 | Brody |
| 5,777,649 A | 7/1998 | Otsuka et al. |
| 5,783,446 A | 7/1998 | Saul et al. |
| 5,789,045 A | 8/1998 | Wapner et al. |
| 5,795,727 A | 8/1998 | Bierre et al. |
| 5,837,200 A | 11/1998 | Diessel et al. |
| 5,858,195 A | 1/1999 | Ramsey |
| 5,876,187 A | 3/1999 | Forster et al. |
| 5,885,470 A | 3/1999 | Parce et al. |
| 5,932,100 A | 8/1999 | Yager et al. |
| 5,976,336 A * | 11/1999 | Dubrow et al. ................ 204/453 |
| 5,979,664 A | 11/1999 | Brodeur |
| 5,988,522 A | 11/1999 | Glezer et al. |
| 5,998,212 A | 12/1999 | Corio et al. |
| 6,033,191 A | 3/2000 | Kamper et al. |
| 6,046,056 A | 4/2000 | Parce et al. |
| 6,048,328 A | 4/2000 | Haller et al. |
| 6,048,734 A | 4/2000 | Burns et al. |
| 6,057,111 A | 5/2000 | Deiss et al. |
| 6,062,681 A | 5/2000 | Field et al. |
| 6,068,752 A | 5/2000 | Dubrow et al. |
| 6,086,740 A | 7/2000 | Kennedy |
| 6,102,530 A | 8/2000 | Kim et al. |
| 6,120,666 A | 9/2000 | Jacobson et al. |
| 6,145,247 A | 11/2000 | McKinnis |
| 6,152,181 A | 11/2000 | Wapner et al. |
| 6,196,525 B1 | 3/2001 | Ganan-Calvo |
| 6,203,291 B1 | 3/2001 | Stemme et al. |
| 6,214,556 B1 | 4/2001 | Olek et al. |
| 6,221,654 B1 | 4/2001 | Quake et al. |
| 6,273,553 B1 | 8/2001 | Kim et al. |
| 6,280,967 B1 | 8/2001 | Ransom et al. |
| 6,318,970 B1 | 11/2001 | Backhouse |
| 6,337,740 B1 | 1/2002 | Parce |
| 6,360,775 B1 | 3/2002 | Barth et al. |
| 6,431,212 B1 | 8/2002 | Hayenga et al. |
| 6,432,630 B1 | 8/2002 | Blankenstein |
| 6,454,862 B1 | 9/2002 | Yoshida et al. |
| 6,455,280 B1 | 9/2002 | Edwards et al. |
| 6,481,453 B1 * | 11/2002 | O'Connor et al. ........ 137/15.04 |
| 6,482,652 B2 | 11/2002 | Furlong et al. |
| 6,507,391 B2 | 1/2003 | Riley et al. |
| 6,524,790 B1 | 2/2003 | Kopf-Sill et al. |
| 6,532,061 B2 | 3/2003 | Ortyn et al. |
| 6,540,895 B1 | 4/2003 | Spence et al. |
| 6,561,224 B1 | 5/2003 | Cho |
| 6,592,821 B1 | 7/2003 | Wada et al. |
| 6,597,438 B1 | 7/2003 | Cabuz et al. |
| 6,629,820 B2 | 10/2003 | Kornelsen |
| 6,657,730 B2 | 12/2003 | Pfau et al. |
| 6,739,576 B2 | 5/2004 | O'Connor et al. |

(56) References Cited

U.S. PATENT DOCUMENTS

| | | | |
|---|---|---|---|
| 6,799,681 B1 | 10/2004 | Warren | |
| 6,802,342 B2 | 10/2004 | Fernandes et al. | |
| 6,803,194 B1 | 10/2004 | Keck et al. | |
| 6,808,075 B2 | 10/2004 | Bohm et al. | |
| 6,821,484 B1 | 11/2004 | Gregersen | |
| 6,830,936 B2* | 12/2004 | Anderson | B01F 11/0071 422/504 |
| 6,877,528 B2 | 4/2005 | Gilbert et al. | |
| 6,976,590 B2 | 12/2005 | Deshpande et al. | |
| 7,024,281 B1 | 4/2006 | Unno | |
| 7,069,943 B2 | 7/2006 | Gilbert et al. | |
| 7,075,652 B1 | 7/2006 | Sarvazyan et al. | |
| 7,080,664 B1* | 7/2006 | Ayer | F15C 1/008 137/826 |
| 7,104,405 B2 | 9/2006 | Bohm et al. | |
| 7,118,910 B2 | 10/2006 | Unger et al. | |
| 7,157,274 B2 | 1/2007 | Bohm et al. | |
| 7,157,275 B2 | 1/2007 | Guarino et al. | |
| 7,220,594 B2 | 5/2007 | Foster et al. | |
| 7,258,774 B2 | 8/2007 | Chou et al. | |
| 7,303,727 B1 | 12/2007 | Dubrow et al. | |
| 7,355,699 B2 | 4/2008 | Gilbert et al. | |
| 7,389,879 B2 | 6/2008 | Tyvoll et al. | |
| 7,452,725 B2* | 11/2008 | Leary et al. | 436/63 |
| 7,497,334 B2 | 3/2009 | Tyvoll et al. | |
| 7,569,788 B2 | 8/2009 | Deshpande et al. | |
| 7,584,857 B2* | 9/2009 | Bohm et al. | 209/155 |
| 7,612,355 B2 | 11/2009 | Wu et al. | |
| 7,820,427 B2 | 10/2010 | Unger et al. | |
| 7,863,035 B2 | 1/2011 | Clemens et al. | |
| 7,963,399 B2 | 6/2011 | Bohm et al. | |
| 7,964,078 B2 | 6/2011 | Lee et al. | |
| 8,123,044 B2* | 2/2012 | Johnson et al. | 209/559 |
| 8,210,209 B2 | 7/2012 | Gilbert et al. | |
| 8,252,604 B2 | 8/2012 | Rigler | |
| 8,268,245 B2 | 9/2012 | Wahl | |
| 8,408,399 B2 | 4/2013 | Bohm et al. | |
| 8,567,608 B2 | 10/2013 | Deshpande et al. | |
| 8,609,039 B2 | 12/2013 | Zhou et al. | |
| 8,623,294 B2 | 1/2014 | Asogawa et al. | |
| 8,623,295 B2 | 1/2014 | Gilbert et al. | |
| 8,678,192 B1 | 3/2014 | Pung et al. | |
| 8,691,164 B2* | 4/2014 | Butler et al. | 422/505 |
| 8,723,140 B2 | 5/2014 | Kiesel et al. | |
| 8,727,131 B2 | 5/2014 | Desphande et al. | |
| 8,844,571 B2* | 9/2014 | Golling | B64C 21/025 137/487.5 |
| 8,895,311 B1* | 11/2014 | Handique | B01J 19/0093 422/502 |
| 9,011,797 B2 | 4/2015 | Gilbert et al. | |
| 9,074,978 B2 | 7/2015 | Lo et al. | |
| 9,149,806 B2* | 10/2015 | Collins | G01N 15/1031 |
| 9,194,786 B2* | 11/2015 | Foster | B01L 3/502761 |
| 9,339,850 B2 | 5/2016 | Deshpande et al. | |
| 9,448,157 B2 | 9/2016 | Ito | |
| 9,550,215 B2 | 1/2017 | Deshpande et al. | |
| 2002/0005354 A1 | 1/2002 | Spence et al. | |
| 2002/0058332 A1 | 5/2002 | Quake et al. | |
| 2002/0093641 A1 | 7/2002 | Ortyn et al. | |
| 2002/0166585 A1 | 11/2002 | O'Connor et al. | |
| 2003/0027225 A1 | 2/2003 | Wada et al. | |
| 2004/0037739 A1* | 2/2004 | McNeely et al. | 422/58 |
| 2004/0180426 A1 | 9/2004 | Maher et al. | |
| 2004/0233424 A1 | 11/2004 | Lee et al. | |
| 2006/0170912 A1 | 8/2006 | Mueth et al. | |
| 2006/0177348 A1* | 8/2006 | Yasuda et al. | 422/73 |
| 2006/0278288 A1 | 12/2006 | Gilbert et al. | |
| 2007/0065808 A1 | 3/2007 | Bohm et al. | |
| 2008/0070311 A1* | 3/2008 | Li | 436/63 |
| 2008/0213821 A1 | 9/2008 | Liu et al. | |
| 2009/0283452 A1* | 11/2009 | Lean et al. | 209/155 |
| 2010/0032350 A1 | 2/2010 | Deshpande et al. | |
| 2010/0133151 A1 | 6/2010 | Bohm et al. | |
| 2011/0005978 A1 | 1/2011 | Bohm et al. | |
| 2011/0030808 A1 | 2/2011 | Chiou et al. | |
| 2012/0006727 A1 | 1/2012 | Bohm et al. | |
| 2012/0012508 A1* | 1/2012 | Deshpande et al. | 209/10 |
| 2012/0015442 A1 | 1/2012 | Gilbert et al. | |
| 2012/0153185 A1 | 6/2012 | Ito et al. | |
| 2012/0258488 A1 | 10/2012 | Abilez et al. | |
| 2013/0083315 A1* | 4/2013 | Lo et al. | 356/73 |
| 2014/0251879 A1 | 9/2014 | Deshpande et al. | |
| 2014/0339445 A1 | 11/2014 | Sharpe et al. | |
| 2015/0298122 A1 | 10/2015 | Zeng et al. | |
| 2015/0352597 A1 | 12/2015 | Deshpande et al. | |
| 2015/0375227 A1* | 12/2015 | Quake | B01L 3/502784 422/502 |
| 2016/0040226 A1 | 2/2016 | Mehta et al. | |
| 2016/0158758 A1 | 6/2016 | Johnson et al. | |

FOREIGN PATENT DOCUMENTS

| | | |
|---|---|---|
| EP | 1065378 A2 | 1/2001 |
| GB | 2229649 A | 10/1990 |
| JP | S49-046274 | 5/1974 |
| JP | S61-137062 A | 6/1986 |
| JP | S63-259466 A | 10/1988 |
| JP | H01-170853 A | 7/1989 |
| JP | H03-043070 | 2/1991 |
| JP | H05-506180 A | 9/1993 |
| JP | H06-507241 | 8/1994 |
| JP | H08-332074 A | 12/1996 |
| JP | H09-141124 A | 6/1997 |
| JP | H11-508182 A | 7/1999 |
| JP | 2001-521755 A | 11/2001 |
| JP | 2002-503334 A | 1/2002 |
| JP | 2004-505272 A | 2/2004 |
| WO | 91/14505 A1 | 10/1991 |
| WO | 91/15750 A1 | 10/1991 |
| WO | 98/07069 A1 | 2/1998 |
| WO | 98/10267 A1 | 3/1998 |
| WO | 98/52691 A1 | 11/1998 |
| WO | 99/23471 A1 | 5/1999 |
| WO | 0070080 A1 | 11/2000 |
| WO | 02/10713 A2 | 2/2002 |
| WO | 02/44689 A2 | 6/2002 |
| WO | 2003089158 A1 | 10/2003 |

OTHER PUBLICATIONS

Communication issued in European Application No. 03 726 391.0-2204, dated Apr. 12, 2010.
Supplementary European Search Report issued in European Application No. 03726391.0-2204, dated Oct. 6, 2009.
Office Action issued in Chinese Application No. 03814212.0, dated Feb. 20, 2009.
Office Action issued in Chinese Application No. 03814212.0, dated Apr. 25, 2008.
Office Action in Japanese Application No. 2004-536583, dated Sep. 29, 2009.
Written Opinion issued in Singapore Application No. 200701943-3, dated Dec. 1, 2009.
International Preliminary Examination Report issued in International Application No. PCT/US03/29198, dated Feb. 21, 2006.
International Search Report issued in International Application No. PCT/US03/29198, dated Jun. 10, 2005.
International Preliminary Examination Report issued in International Application No. PCT/US03/12368, dated Aug. 25, 2004.
International Search Report issued in International Application No. PCT/US03/12368, dated Aug. 21, 2003.
Supplementary European Search Report issued in European Application No. 03752432.9, dated Aug. 14, 2009.
International Preliminary Examination Report issued in International Application No. PCT/US03/12359, dated Nov. 12, 2003.
International Search Report issued in International Application No. PCT/US03/12359, dated Jun. 28, 2003.
Examination Report issued in Australian Application No. 2003228630, dated Feb. 11, 2008.
First Office Action issued in Chinese Application No. 03825178.7, dated Jun. 27, 2008.

(56) References Cited

OTHER PUBLICATIONS

Second Office Action issued in Chinese Application No. 03825178. 7, dated Mar. 20, 2009.
Third Office Action issued in Chinese Application No. 03825178.7, dated Sep. 18, 2009.
Office Action issued in Japanese Application No. 2007-315437, dated May 11, 2011.
Office Action issued in Canadian Application No. 2,482,869, dated Dec. 17, 2010.
Office Action issued in Canadian Application No. 2,482,869, dated Feb. 16, 2010.
Examination Report issued in Indian Application No. 1587/KOLNP/2004, dated Jul. 15, 2010.
Office Action issued in Japanese Application No. 2007-315437, dated May 12, 2010.
Examination Report issued in Australian Application No. 2010200179, dated Mar. 22, 2011.
Office Action issued in Israeli Application No. 167266, dated Sep. 28, 2010.
Office Action issued in Japanese Application No. 2003-585899, dated Jan. 11, 2008.
Office Action issued in Japanese Application No. 2003-585899, dated Jun. 6, 2007.
Office Action issued in Canadian Application No. 2,482,869, dated Sep. 13, 2011.
Office Action issued in Chinese Application No. 200910168699.1, dated Jun. 21, 2012.
Office Action issued in U.S. Appl. No. 12/821,790, dated Oct. 1, 2012.
Office Action issued in U.S. Appl. No. 13/425,132, dated Nov. 6, 2012.
International Preliminary Examination Report issued in International Application No. PCT/US03/12360, dated Jul. 21, 2004.
International Search Report issued in International Application No. PCT/US03/12360, dated Oct. 30, 2003.
Notice of Allowance issued in U.S. Appl. No. 12/821,790, dated Apr. 14, 2015.
Notice of Allowance issued in U.S. Appl. No. 13/245,132, dated Jan. 2, 2014.
Office Action issued in U.S. Appl. No. 10/329,008, dated May 23, 2005.
Office Action issued in U.S. Appl. No. 10/329,008, dated Nov. 30, 2004.
Office Action issued in U.S. Appl. No. 10/664,587, dated Feb. 9, 2006.
Office Action issued in U.S. Appl. No. 10/664,587, dated Jun. 13, 2005.
Office Action issued in U.S. Appl. No. 10/664,587, dated Nov. 30, 2004.
Office Action issued in U.S. Appl. No. 11/101,038, dated Feb. 22, 2008.
Office Action issued in U.S. Appl. No. 11/101,038, dated Jul. 9, 2007.
Office Action issued in U.S. Appl. No. 11/101,038, dated Jun. 5, 2006.
Office Action issued in U.S. Appl. No. 12/499,254, dated Jan. 11, 2012.
Office Action issued in U.S. Appl. No. 12/499,254, dated Jul. 26, 2012.
Office Action issued in U.S. Appl. No. 12/499,254, dated Mar. 9, 2010.
Office Action issued in U.S. Appl. No. 12/821,790, dated Dec. 2, 2013.
Office Action issued in U.S. Appl. No. 12/821,790, dated Jun. 6, 2012.
Office Action issued in U.S. Appl. No. 12/821,790, dated Oct. 1, 2014.
Office Action issued in U.S. Appl. No. 13/245,132, dated Jun. 10, 2013.
Office Action issued in U.S. Appl. No. 13/245,132, dated Nov. 6, 2012.
Office Action issued in U.S. Appl. No. 14/281,303, dated Apr. 18, 2016.
Office Action issued in U.S. Appl. No. 11/603,444, dated Dec. 23, 2009.
Office Action issued in U.S. Appl. No. 12/537,802 dated Jun. 18, 2010.
Search Information Statement issued in Australian Application No. 2010200179, dated Mar. 22, 2011.
Examination Report by Brazilian Patent Office for Brazilian Application No. PI0309321-2 dated Aug. 9, 2016 (English translation).

* cited by examiner

METHOD AND APPARATUS FOR SORTING PARTICLES

RELATED APPLICATIONS

This application is a continuation of U.S. patent application Ser. No. 13/158,960, filed Jun. 13, 2011 and entitled "METHOD AND APPARATUS FOR SORTING PARTICLES," which is a continuation of U.S. patent application Ser. No. 12/537,802, filed Aug. 7, 2009, which is a continuation of U.S. patent application Ser. No. 11/499,953, filed Aug. 7, 2006, which is a continuation of U.S. patent application Ser. No. 10/940,143 entitled "Method and Apparatus for Sorting Particles" filed Sep. 13, 2004, which is a divisional of U.S. patent application Ser. No. 10/179,488 entitled "Method and Apparatus for Sorting Particles" filed Jun. 24, 2002 which claims priority to U.S. Provisional Patent Application Ser. No. 60/373,256 entitled "Microfluidic System Including a Bubble Valve for Regulating Fluid Flow Through a Microchannel" filed Apr. 17, 2002, the contents of each application is incorporated herein by reference in their entirety.

FIELD OF THE INVENTION

The invention relates to a method and apparatus for the sorting of particles in a suspension, where the input flow path of a sorting module can be split into several output channels. More particular, the invention relates to a particle sorting system in which a plurality of sorting modules are interconnected as to yield an increased particle throughput.

BACKGROUND OF THE INVENTION

In the fields of biotechnology, and especially cytology and drug screening, there is a need for high throughput sorting of particles. Examples of particles that require sorting are various types of cells, such as blood platelets, white blood cells, tumorous cells, embryonic cells and the like. These particles are especially of interest in the field of cytology. Other particles are (macro) molecular species such as proteins, enzymes and poly-nucleotides. This family of particles is of particular interest in the field of drug screening during the development of new drugs.

Methods and apparatuses for particle sorting are known, and the majority described in the prior art work in the condition where the particles are suspended in a liquid flowing through a channel network having at least a branch point downstream and are operated according the detect-decide-deflect principle. The moving particle is first analyzed for a specific characteristic, such as optical absorption, fluorescent intensity, size etc. Depending on the outcome of this detection phase, it is decided how the particle will be handled further with. The outcome of the decision is then applied to deflect the direction of specific particle towards a predetermined branch of the channel network.

Of importance is the throughput of the sorting apparatus, i.e. how many particles can be sorted per unit of time. Typical sorting rates for sorters employing flows of particle suspension in closed channels are in the range from a few hundred particles per second to thousands of particles per second, for a single sorting unit.

An example of a sorting device is described in U.S. Pat. No. 4,175,662, the contents of which are herein incorporated by reference. In the '662 patent, a flow of particles, cells in this case, flows through the center of a straight channel, which branches into two perpendicular channels at a branching point downstream (T-branch). The entering particles are surrounded by a sheath of compatible liquid, keeping the particles confined to the center of the channel. In normal conditions, the flow ratio through the two branches is adjusted so that the particles automatically flow through one of the branches. In a section of the channel a characteristic of the particles is determined using a detector, which can be an optical system (detection phase). The detector raises a signal, which is interpreted. When the detector detects a particle possessing a predetermined characteristic in the decision phase, a deflector is activated for deflecting the particle in a deflection phase. In this case, the deflector comprises an electrode pair, positioned in the branch of the channel where the particles normally flow through in the inactivated state of the deflector. By the application of current pulses, the aqueous liquid is electrolysed, yielding a gas bubble evolving between the electrode pair. As the gas bubble increases in size, the flow rate through this branch is reduced during the evolving phase. After the current pulse is applied, the bubble growth stops and the gas bubble is carried along with the flow. As a result, the flow through the specific branch is momentarily reduced and the particle of interest changes paths and flows down the other branch.

The described device is effective for sorting particles, however one serious drawback is that gas bubbles are created which potentially can accumulate at certain points of the fluidic network or clog flow channels, yielding erroneous sorting. Another drawback is that the generated gasses (mostly oxygen and hydrogen) and ionic species (mostly $OH^-$ and $H^+$) influence the particles flowing through the branch with the electrode pair. In addition, cells and delicate proteins such as enzymes are very fragile and can be destroyed by the fouling constituents co-generated with the gas bubble. Another drawback is the complexity of the overall sorting apparatus. In particular, the micro electrode construction is very complex to mount and assemble in the small channels of the system. As a result, the cost of a sorting unit is relatively large.

Another example of a particle sorting system of the prior art is disclosed in U.S. Pat. No. 3,984,307, the contents of which are herein incorporated by reference. In the '307 patent, the particles are flowing, confined by a flowing sheath liquid, through the center of a channel. After passing a detector section, the channel branches to two channels under an acute angle (Y-branch). Just before the branching point, an electrically activated transducer is located in the channel for deflecting a specific particle having an appropriate, predetermined characteristic. The transducer described is a piezo actuator or ultrasonic transducer, yielding upon electrical activation a pressure wave in the channel. The generated pressure wave momentarily disturbs the flow in one branch thus deflecting the particle of interest into the other branch Also in this device, as in the previous discussed device, the deflector is incorporated within the channel system, resulting in relatively large costs of construction. Another drawback is the deflector principle used. The generated pressure waves are not confined to the branching point, but will propagate upstream into the detector section as well as downstream both branches and influence the overall flow through the channel. This is particularly a drawback if sorters of this type are connected either in series or in parallel as to build a sorter system with increased throughput. Pressure waves generated in one sorter can then influence the flows and deflection of particles in neighboring sorter units.

Another disclosed sorter, U.S. Pat. No. 4,756,427, the contents of which are herein incorporated by reference, is analogous to the sorter disclosed the earlier discussed '662. In this case however, the flow in one branch is disturbed by momentarily changing the resistance of the branch. The resistance is changed by changing the height of the branch channel by an external actuator. In the preferred embodiment, this external actuator is a piezo disc glued on top of the channel, causing it to move downwards upon activation.

Although the construction of the sorter described in the '427 patent is less complex as the previous sorter structures, it is still problematic to couple multiple sorter modules of the described type together to increase the sorting rate. This is, as in the sorter described in '307 because of the generated pressure waves causing interference with other sorter modules.

Another particle sorting device is described in U.S. Pat. No. 5,837,200, the contents of which are herein incorporated by reference. The '200 patent describes a sorting device that uses a magnetic deflection module to classify or select particles based on their magnetic properties. The '200 patent further describes processing and separating individual particle streams in parallel.

SUMMARY OF THE INVENTION

The present invention provides a method and apparatus for sorting particles moving through a closed channel system of capillary size. The particle sorting system of the invention provides a sorting module that can be assembled at low cost while providing an accurate means of sorting large amounts of particles per unit of time. The particle sorting system may include a plurality of closely coupled sorting modules which are combined to further increase the sorting rate. The particle sorting system may comprise a multi-stage sorting device for serially sorting streams of particles, in order to decrease the error rate.

The particle sorting system implements an improved fluidic particle switching method and switching device according to the current invention. The particle sorting system comprises a closed channel system of capillary size for sorting particles. The channel system comprises a first supply duct for introducing a stream of particles and a second supply duct for supplying a carrier liquid. The first supply duct forms a nozzle to introduce a stream of particles into the flow of carrier liquid. The first supply duct and the second supply duct enter a measurement duct, which branches into a first branch and a second branch at a branch point. A measurement region is defined in the measurement duct and is associated with a detector to sense a predetermined characteristic of particles in the measurement region. Two opposed bubble valves are positioned in communication with the measurement duct and are spaced opposite each other. The bubble valves communicate with the measurement duct through a pair of opposed side passages. Liquid is allowed to partly fill these side passages to form a meniscus therein which interfaces the carrier liquid with the reservoir of the bubble valves. An external actuator is also provided for actuating one of the bubble valves. When the external actuator is activated, the pressure in the reservoir of the activated bubble valve increases, deflecting the meniscus and causing a flow disturbance in the measurement duct to deflect the flow therein.

When a sensing means in the measuring region senses a predetermined characteristic in a particle flowing through the measurement region, the sensing means produces a signal in response to the sensed characteristic. The external actuator is responsive to the sensing means to cause a pressure pulse in a compression chamber of a first bubble valve to deflect the particle with the predetermined characteristic, causing the selected particle to flow down the second branch duct.

In one aspect, the invention comprises a method of sorting particles including the steps of providing a measurement duct having an inlet and a branching point at which the duct separates into two branch ducts, conducting a stream of fluid into the duct inlet with a stream of particles suspended therein, such that the particles normally flow through a first one of the branch ducts and providing upstream from the branching point two opposing side passages for momentarily deflecting the stream in the duct. A first one of the side passages is hydraulically connected to a compression chamber of a first bubble valve, which is acted upon by an external actuator for varying the pressure therein. A second of the side passages is hydraulically connected with a buffer chamber of a second bubble valve for absorbing pressure variations. The method further comprises providing a measurement station along the measurement duct upstream of the side passages for sensing a predetermined characteristic of particles in the stream and for producing a signal when the predetermined characteristic is sensed. The method further comprises the step of, in response to sensing the predetermined characteristic, activating the external actuator for creating a flow disturbance in the duct between the side passages, thereby deflecting the particle having the predetermined characteristics and causing the selected particle to flow down the second branch duct.

In further aspects of the invention, the particle sort rate is respectively increased or the type of particles sorted being increased, by respectively connecting a plurality of sorting modules in parallel or serially connecting a plurality of sorting modules in a binary tree like configuration.

According to one aspect of the invention, a particle sorting system is provided. The particles sorting system comprises a first duct for conveying a stream of suspended particles confined in a carrier liquid, comprising an inlet, a first outlet and a second outlet, a sensor for sensing a predetermined characteristic in a particle, a side channel in communication with the first duct, a sealed chamber positioned adjacent to the side channel, wherein the carrier fluid forms a meniscus in the side channel to separate the sealed chamber from the carrier fluid; and an actuator. The actuator modifies the pressure in the sealed chamber to deflect the meniscus when the sensor senses the predetermined characteristic. The deflection of the meniscus causes the particle having the predetermined characteristic to flow into the second outlet while particles that do not have the predetermined characteristic flow into the first outlet.

According to another aspect of the invention, a particle sorting system is provided. The particle sorting system comprises a first duct for conveying a stream of suspended particles confined in a carrier liquid, a sensor for sensing a predetermined characteristic in a particle and a first side channel in communication with the first duct. The first duct comprises an inlet, a first outlet and a second outlet. The particle sorting system further comprises a sealed actuator chamber positioned adjacent to the first side channel, wherein the carrier fluid forms a meniscus in the first side channel to separate the sealed chamber from the carrier fluid, an actuator for modifying the pressure in the sealed actuator chamber to deflect the meniscus when the sensor senses said predetermined characteristic and a buffer. The deflection of the meniscus creates a transient flow in the first duct which deflects particle having said predetermined characteristic to flow into the second outlet while particles that do not have said predetermined characteristic flow into the first outlet. The buffer absorbs a transient flow in the first duct.

According to another aspect of the invention, a particle sorting system is provided. The particle sorting system comprises a duct for conveying a stream of particles in a carrier fluid, a sensor for sensing a predetermined characteristic in a particle and an actuator. The duct comprises an inlet, a first outlet and a second outlet, wherein the particles normally flow from the inlet into the first outlet. The actuator selectively applies a pressure pulse to the suspension to deflect a particle in the stream of particles into the second outlet when said predetermined characteristic is detected. The particle sorting system further comprises a buffer for absorbing the pressure pulse.

According to yet another aspect of the invention, a particle sorting system is provided. The particle sorting system comprises a duct for conveying a stream of suspended particles confined in a carrier fluid, comprising an inlet, a first outlet and a second outlet, wherein the particles normally flow from the inlet into the first outlet, a sensor for sensing a predetermined characteristic in a particle, an actuator for selectively applying a pressure pulse to the stream of suspended particles to deflect a particle in the stream of particles when said predetermined characteristic is detected, causing it to flow into the second outlet and a buffer for absorbing the pressure pulse. The buffer comprises a side channel in communication with the duct, a sealed buffer chamber adjacent to the side channel and a meniscus formed by the carrier fluid at an interface between the sealed chamber and the side channel.

According to still another aspect of the invention, a particle sorting system is provided. The particle sorting system comprises a first duct for conveying a stream of suspended particles confined in a carrier liquid, comprising an inlet, a first outlet and a second outlet, a sensor for sensing a predetermined characteristic in a particle, a side channel in communication with the first duct, a sealed chamber positioned adjacent to the side channel, wherein the carrier fluid forms a first meniscus in the side channel to separate the sealed chamber from the sealed chamber an actuator for modifying the pressure in the sealed chamber to deflect the first meniscus when the sensor senses said predetermined characteristic, whereby the deflection of the meniscus causes a particle having said predetermined characteristic to flow into the second outlet while particles that do not have said predetermined characteristic flow into the first outlet and a buffer for absorbing the pressure pulse. The buffer comprises a side channel in communication with the duct, a sealed chamber adjacent to the side channel and a first meniscus formed by the carrier fluid at an interface between the sealed chamber and the side channel.

According to another aspect of the invention, a particle sorting system for sorting particles suspended in a liquid is provided. The particle sorting system comprises an inlet duct through which flows a liquid containing particles having a predetermined characteristic and particles not having a predetermined characteristic. The inlet duct branches into a plurality of measurement channels which are operated in parallel and simultaneously fed with the liquid, each measurement channel having a sorting module and two outlet channels, and each sorting module having a switch unit for distribution of particles having a predetermined characteristic and particles not having a predetermined characteristic to said two different outlet channel. Each switch unit comprises at least one sensor which detects and classifies the particles having the predetermined characteristic, a side passage in communication with the inlet duct, a sealed chamber adjacent to and separated from the side passage by a meniscus formed by the liquid and an actuator controlled by each said sensor arranged on each said switch unit for selectively deflecting the meniscus to deflect a particle having the predetermined characteristic into one of said outlet channel. Each of the two outlet channels on each measurement channel is connected to a separate summing channel for the particles having a predetermined characteristic and particles not having a predetermined characteristic selectively distributed to it.

According to still another aspect of the invention, a particle sorting system for sorting particles suspended in a liquid is provided comprising an inlet duct through which flows a liquid containing particles having a predetermined characteristic and particles not having a predetermined characteristic. The inlet duct branches into a plurality of channels which are operated in parallel and simultaneously fed with the liquid, each channel having a sorting module and two outlet channels, and each sorting module having a switch unit for distribution of particles having a first predetermined characteristic and particles not having the first predetermined characteristic between said two different outlet channels. Each sorting module comprises at least one sensor which detects and classifies the particles having the first predetermined characteristic, and an actuator controlled by each of said sensor arranged on each said switch unit for selectively deflecting a particle having the first predetermined characteristic into one of said outlet channels. Each of said two outlet channels on each sorting module is connected to a separate summing channel for the particles having the first predetermined characteristic and particles not having the first predetermined characteristic selectively distributed to it. The system further comprises at least one secondary sorting module connected to the summing channel for the particles having the first predetermined characteristic, each of said secondary sorting modules having a first outlet channel and a second outlet channel, a detector for sensing particles and a switch unit for selectively deflecting a particle having a second predetermined characteristic into one of said outlet channels based on a second predetermined characteristic.

According to another aspect, a particle sorting system is provided, comprising a plurality of parallel primary sorting channels through which flows a stream of suspended particles confined in a carrier liquid. Each primary sorting channel has a detection region for detecting a predetermined characteristic in a particle and a switching region for separating particles having the predetermined characteristic into a first receiving channel from particles that do not have the predetermined characteristic, which flow into a second receiving channel. The system further comprises an aggregation region for aggregating the particles having the predetermined characteristic from the first receiving channels, and at least one secondary sorting channel in series with the plurality of parallel primary sorting channels for collecting the selected particles from the plurality of first outlet channels and separating particles in the secondary sorting channel having the predetermined characteristic from other particles in the secondary sorting channel.

According to a final aspect, a method of sorting small particles is provided. The method comprises the steps of providing a closed duct having an inlet and a fork at which the duct separates into two branch ducts, conducting a stream of liquid into the duct inlet with a stream of particles suspended therein, the particle stream normally flowing through a first one of the branch ducts surrounding the stream of liquid with a particle free enveloping current of liquid to produce substantially laminar flow and providing a measurement station along the closed duct upstream of the fork for sensing a predetermined property of particles in the stream and for producing a signal when the property is sensed. The method further comprises providing an actuator for applying a pressure on the liquid and providing means for buffering pressure variations in the liquid. The pressure buffering means cooperates with the pressure applying means to result in a momentary deflection of the liquid streaming through the duct substantially perpendicular to the normal direction of flow from the point where the pressure is applied towards the point where the pressure is buffered, causing the specific particle having the predetermined property to flow into the second branch duct without eliminating the laminar flow.

DETAILED DESCRIPTION OF THE INVENTION

The present invention provides a particle sorting system for sorting particles suspended in a liquid. The particle sorting system provides high-throughput, low error sorting of particles based on a predetermined characteristic. The present invention will be described below relative to illustrative embodiments. Those skilled in the art will appreciate that the present invention may be implemented in a number of different applications and embodiments and is not specifically limited in its application to the particular embodiments depicted herein.

Figure 1:
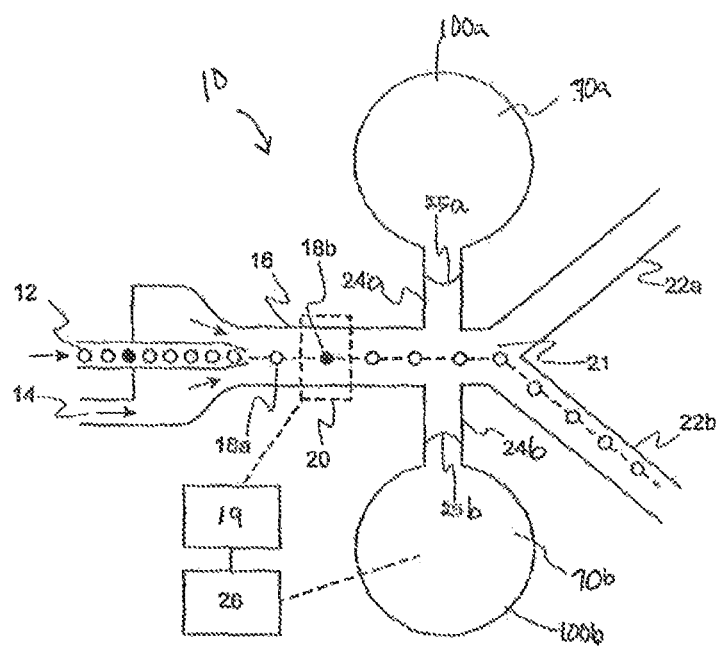
FIG. 1 is a schematic view of a particle sorting system according to an illustrative embodiment of the invention.

FIG. 1 shows a schematic of a particle sorting system according to an illustrative embodiment of the invention. According to one application of the present invention, a particle sorting system 10 comprises a closed channel system of capillary size for sorting particles. The channel system comprises a first supply duct 12 for introducing a stream of particles 18 and a second supply duct 14 for supplying a carrier liquid. The first supply duct 12 forms a nozzle 12a, and a stream of particles is introduced into the flow of carrier liquid. The first supply duct 12 and the second supply duct 14 enter a measurement duct 16 for conveying the particles suspended in the carrier liquid, which branches into a first branch 22a and a second branch 22b at a branch point 21. A measurement region 20 is defined in the measurement duct 16 and is associated with a detector 19 to sense a predetermined characteristic of particles in the measurement region 20. Two opposed of bubble valves 100a and 100b are positioned in communication with the measurement duct 16 and are spaced opposite each other. The bubble valves 100a, 100b communicate with the measurement duct 16 through a pair of opposed side passages 24a and 24b, respectively. Liquid is allowed to partly fill these side passages 24a and 24b to form a meniscus 25 therein. The meniscus defines an interface between the carrier liquid and a gas in the reservoir of the associated bubble valve 100. An external actuator 26 is also provided for actuating the first bubble valves 100a, which momentarily causes a flow disturbance in the duct to deflect the flow therein when activated by the actuator 26. The second bubble valve 100b serves as a buffer for absorbing the pressure pulse created by the first bubble valve 100a.

The first side passage 24a is hydraulically connected to a compression chamber 70a in the first bubble valve 100a, so that if the pressure in this chamber is increased, the flow in the measurement duct near the side passage is displaced inwards, substantially perpendicular to the normal flow in the duct. The second side passage 24b, positioned opposite of the first side passage 24a is hydraulically connected to a buffer chamber 70b in the second bubble valve 100b for absorbing pressure transients. This second side passage 24b co-operates with the first side passage 24a to direct the before mentioned liquid displacement caused by pressurizing the compression chamber 70a, so that the displacement has a component perpendicular to the normal flow of the particles through the measurement duct.

Upon pressurizing the compression chamber 70a an amount of liquid is transiently discharged from the first side passage 24a. The resiliency of the second side passage 24b results upon a pressurized discharge, in a transient flow of the liquid in the duct into the second side passage 24a. The co-operation of the two side passages and the fluidic structures they interconnect causes the flow through the measurement duct 16 to be transiently moved sideways back and forth upon pressurizing and depressurising of the compression chamber 70a induced by the external actuator 26 in response to the signal raised by the detection means 19. This transient liquid displacement, having a component perpendicular to the normal flow in the duct, can be applied in deflecting particles having predetermined characteristics to separate them from the remaining particles in the mixture.

As shown, the measurement duct 16 branches at the branch point 21 into two branches 22a, 22b and the flow rates in these branches are adjusted so that the particles normally stream through the second of the two branches 22b. The angle between the branches 22a, 22b is between 0 and 180 degrees, preferably between 10 and 45 degrees. However, the angle can even be 0 degrees, which corresponds to two parallel ducts with a straight separation wall between them.

The particles to be sorted are preferably supplied to a measurement position in a central fluid current, which is surrounded by a particle free liquid sheath. The process of confining a particle stream is known, and often referred to as a 'sheath flow' configuration. Normally confinement is achieved by injecting a stream of suspended particles through a narrow outlet nozzle into a particle free carrier liquid flowing in the duct 16. By adjusting the ratio of flow rates of the suspension and carrier liquid, the radial confinement in the duct as well as the inter particle distance can be adjusted. A relative large flow rate of the carrier liquid results in a more confined particle stream having a large distance between particles.

In a suspension introduced by the first supply duct 12, two types of particles can be distinguished, normal particles 18a and particles of interest 18b. Upon sensing the predetermined characteristic in a particle 18b in the measurement region 20, the detector 19 raises a signal. The external actuator 26 activates the first actuator bubble valve 100a, when signaled by the detector 19 in response to sensing the predetermined characteristic, to create a flow disturbance in the measurement duct 16 between the side passages 24a, 24b. The flow disturbance deflects the particle 18b having the predetermined characteristic so that it flows down the first branch duct 22a rather than the second branch duct 22b. The detector communicates with the actuator 26, so that when the detector 19 senses a predetermined characteristic in a particle, the actuator activates the first bubble valve 100a to cause pressure variations in the reservoir 70a of the first bubble valve. The activation of the first bubble valves deflects the meniscus 25a in the first bubble valve 100a and causes a transient pressure variation in the first side passage 24a. The second side passage 24b and the second bubble valve 100b absorb the transient pressure variations in the measurement duct 16 induced via the actuator 26. Basically, the reservoir 70b of the second bubble valve 100b is a buffer chamber having a resilient wall or containing a compressible fluid, such as a gas. The resilient properties allow the flow of liquid from the measurement duct into the second side passage 24b, allowing the pressure pulse to be absorbed and preventing disturbance to the flow of the non-selected particles in the stream of particles.

At the measurement region 20, individual particles are inspected, using a suitable sensor means 19, for a particular characteristic, such as size, form, fluorescent intensity etc. Examples of applicable sensing means, known in the art, are various types of optical detection systems such as microscopes, machine vision systems and electronic means for measuring electronic properties of the particles. Particularly well known systems in the field are systems for measuring the fluorescent intensity of particles. These systems comprise a light source having a suitable wavelength for inducing fluorescence and a detection system for measuring the intensity of the induced fluorescent light. This approach is often used in combination with particles that are labelled with a fluorescent marker, i.e. an attached molecule that upon illuminating with light of a particular first wavelength produces light at another particular second wavelength (fluorescence). If this second wavelength light is detected, the characteristic is sensed and a signal is raised.

Other examples include the measurement of light scattered by particles flowing through the measurement region. Interpreting the scattering yield information on the size and form of particles, which can be adopted to raise a signal when a predetermined characteristic is detected.

The actuator 26 for pressurizing the compression chamber of the first bubble valve may comprise an external actuator that responds to a signal from the sensor that a particle has a selected predetermined characteristic. There are two classes of external actuators that are suitable for increasing the pressure. The first class directly provides a gas pressure to the liquid in the first side passage 24a. For example, the actuator may comprise a source of pressurized gas connected with a switching valve to the liquid column in the side passage 24a. Activation of the switch connects the passage to the source of pressurized gas, which deflects the meniscus in the liquid. Upon deactivation, the switch connects the passage 24a back to the normal operating pressure.

Alternatively, a displacement actuator may be used in combination with a closed compression chamber having a movable wall. When the displacement actuator displaces the wall of the compression chamber inward, the pressure inside increases. If the movable wall is displaced back to the original position, the pressure is reduced back to the normal operating pressure. An example of a suitable displacement actuator is an electromagnetic actuator, which causes displacement of a plunger upon energizing a coil. Another example is the use of piezoelectric material, for example in the form of a cylinder or a stack of disks, which upon the application of a voltage produces a linear displacement. Both types of actuators engage the movable wall of the compression chamber 70 to cause pressure variations therein.

Figures 2, 3, 4:
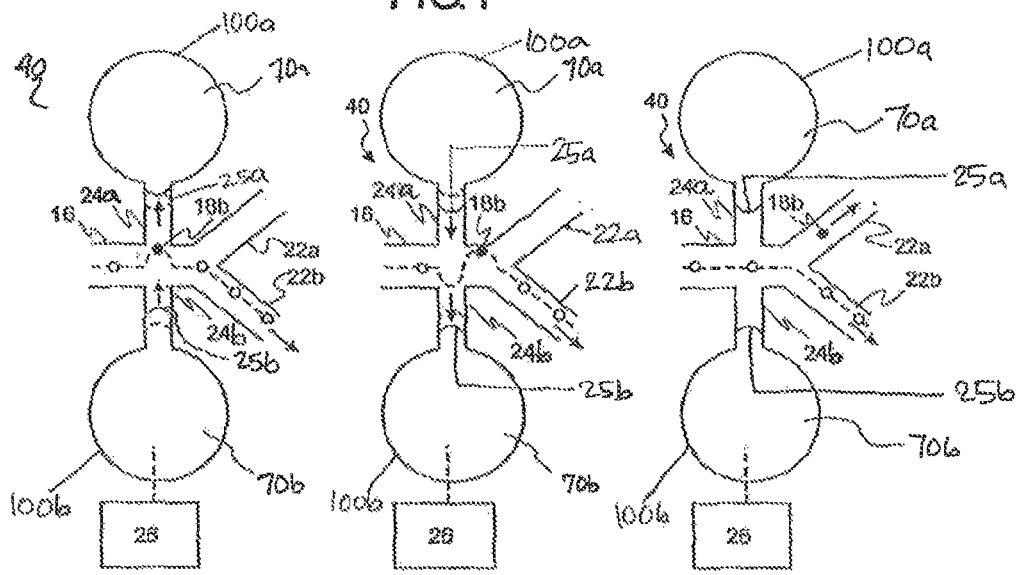
FIGS. 2 through 4 illustrate the operation of the particle sorting system of FIG. 1.

FIGS. 2-4 illustrate the switching operation of switch 40 in the particle sorting system 10 of FIG. 1. In FIG. 2, the detector 19 senses the predetermined characteristic in a particle and raises a signal to activate the actuator 26. Upon activation of the actuator, the pressure within the reservoir 70a of the first bubble valve 100a is increased, deflecting the meniscus 25a and causing a transient discharge of liquid from the first side passage 24a, as indicated by the arrow. The sudden pressure increase caused at this point in the duct causes liquid to flow into the second side passage 24b, because of the resilient properties of the reservoir of the second bubble valve 100b. This movement of liquid into the second side passage 24b is indicated with an arrow. As a result, as can be seen in the figure, the flow through the measurement duct 16 is deflected, causing the selected particle of interest 18b located between the first side passage 24a and the second side passage 24b to be shifted perpendicular to its flow direction in the normal state. The flow resistances to the measurement duct 16, the first branch 22a and the second branch 22b is chosen so that the preferred direction of the flow to and from the first side passage 24a and the second side passage 24b has an appreciable component perpendicular to the normal flow through the measurement duct 16. This goal can for instance be reached by the first branch 22a and the second branch 22b so that their resistances to flow is large in comparison with the flow resistances of the first side passage 24a and the second side passage 24b.

FIG. 3 shows the particle sorting system 10 during the relief of the first bubble valve reservoir when the particle of interest 18b has left the volume between the first side passage 24a and the second side passage 24b. The actuator 26 is deactivated, causing the pressure inside the reservoirs 70a, 70b to return to the normal pressure. During this relief phase there is a negative pressure difference between the two reservoirs 70a, 70b of the bubble valves, causing a liquid flow through the first side passage 24a and the second side passage 24b opposite to the liquid flow shown in the previous figure and as indicated by the arrows.

FIG. 4 illustrates the particle sorting system 10 after completion of the switching sequence. The pressures inside the reservoirs of the bubble valves are equalized, allowing the flow through the measurement duct 16 to normalize. As the particle of interest 18b has been displaced radially, it will flow into the first branch 22a, while the other particle continue to flow into the second branch 22b, thereby separating the particles based on the predetermined characteristic.

This process of detecting and selective deflecting of particles may be repeated many times per second for sorting particles at a high rate. Adopting the fluid switching as described, switching operations may be executed up to around several thousand switching operations per second, yielding sorting rates in the order of million sorted particles per hour.

Figure 5:
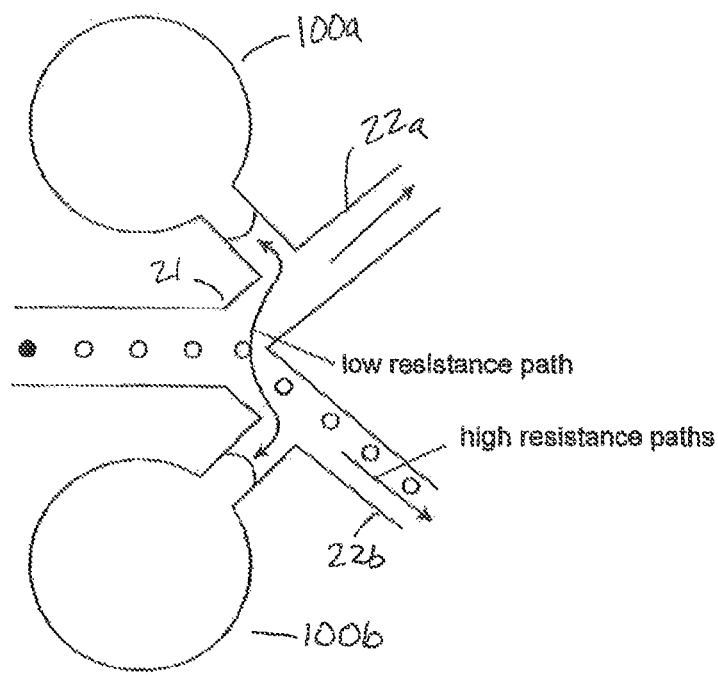
FIG. 5 illustrates a particle sorting system showing alternate positions for the actuator chamber and the buffer chamber.

According to another embodiment of the invention, the actuator bubble valve 100a and the buffer bubble valve 100b may be placed in different positions. For example, as shown in FIG. 5, the actuator bubble valve 100a and the first side passage 24a and/or the buffer bubble valve 100b and the second side passage 24b may be place upstream from the branch point 21. The components may be placed in any suitable location, such that the flow resistance between the actuator chamber 70a and the buffer chamber 70b is less than the flow resistance between any of these latter components and other pressure sources. More particularly, the actuator chamber 70a and the buffer chamber 70b may be placed such that the flow resistance between them is less than the flow resistance between a selected particle and a subsequent particle in the stream of particles. The positioning of the components in this manner thus prevents a pressure wave generated by the above described method of deflecting a single selected particle, from travelling upstream or downstream and affecting the flow of the remaining particles in the stream of particles. The larger the difference in flow resistances, the larger the level of isolation of the fluidic switching operation with associated pressure transients from the flow characteristics in the rest of the system. Moreover, the in-situ dampening of generated pressure pulses applied for sorting allows the implementation of sorting networks comprising a plurality of switches 40, each of which is hydraulically and pneumatically isolated from the others.

Figure 6:
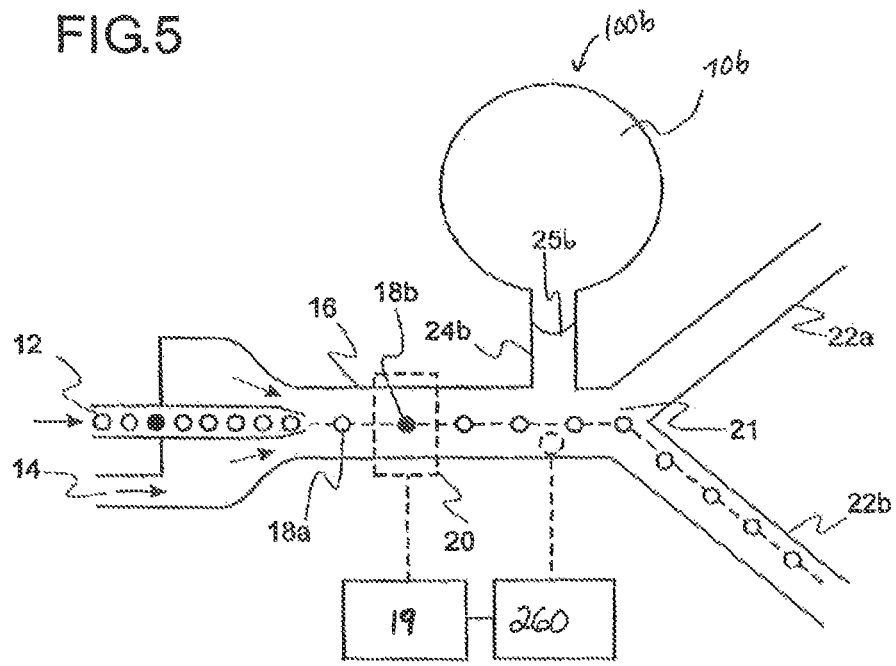
FIG. 6 illustrates the particle sorting system according to another embodiment of the invention.

According to another embodiment, shown in FIG. 6, the particle sorting system of the invention may use any suitable pressure wave generator (in place of a bubble valve) in combination with the buffer bubble valve 100b. For example, the pressure wave generator 260 may comprise an actuator such as a piezoelectric column or a stepper motor, provided with a plunger that can act upon the flowing liquid, either directly or via deflection of the channel system, to selectively deflect particles when the actuator is activated by a signal. Other suitable pressure wave generators include electromagnetic actuators, thermopneumatic actuators and a heat pulse generator for generating vapor bubbles in the flowing liquid by applying heat pulses. The buffer bubble valve 100b is positioned to absorb the pressure wave created by the pressure wave generator 260 to prevent flow disturbance in the other particles of the particle stream. The spring constant of the buffer 100b may be varied according to the particular requirements by varying the volume of the buffer chamber 70b, the cross-sectional area of the side passage 24b and/or the stiffness or the thickness of a flexible membrane (reference 72 in FIG. 7) forming the buffer chamber 70b.

Figure 7:
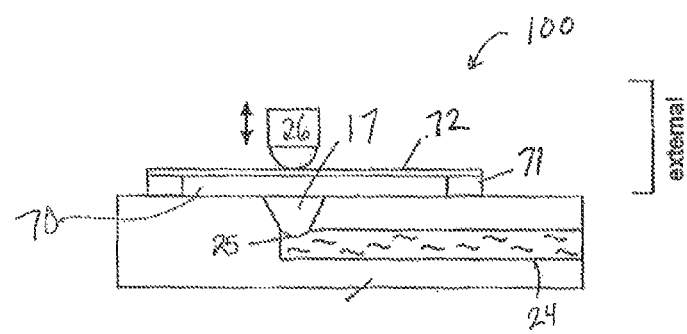
FIG. 7 illustrates a bubble valve suitable for use in the particle sorting system of the invention.

FIG. 7 illustrates an embodiment of a bubble valve 100 suitable for creating a pressure pulse to separate particles of interest from other particles in a stream of particles and/or acting as a buffer for absorbing a pressure pulse according to the teachings of the present invention. As shown, the bubble valve 100 is formed adjacent to a side passage 24a or 24b formed in a substrate which leads to the measurement duct 16. The side passage 24a includes a fluid interface port 17 formed by an aperture in the side wall of the passage. A sealed compression chamber 70 is positioned adjacent to the side passage 24a and communicates with the side passage through the fluid interface port. The illustrative chamber 70 is formed by a seal 71 and a flexible membrane 72. The carrier fluid in the side passage 24a forms a meniscus 25 at the interface between the side passage and the chamber. The actuator 26 depresses the flexible membrane to increase the pressure in the chamber, which deflects the meniscus and causes a pressure pulse in the carrier fluid.

Figure 8:
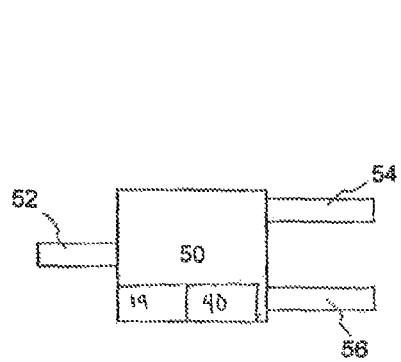
FIG. 8 is a schematic diagram of the particle sorting system of an illustrative embodiment of the invention

FIG. 8 shows a sorting module 50 having an appropriate supply duct 52 for providing a stream of particles to be sorted as well as an outlet duct 54 and a second outlet duct 56 carrying the particles sorted in the sorting module 50. The sorting module 50 comprises detector system 19 for sensing particles entering the sorting module 50 via the supply duct 52 operationally connected to a switch 40 for providing the required switching capabilities to sort particles. The first branch 22b and second branch 22a are in fluidic connection with the outlet duct 54 and second outlet duct 56.

Figure 9:
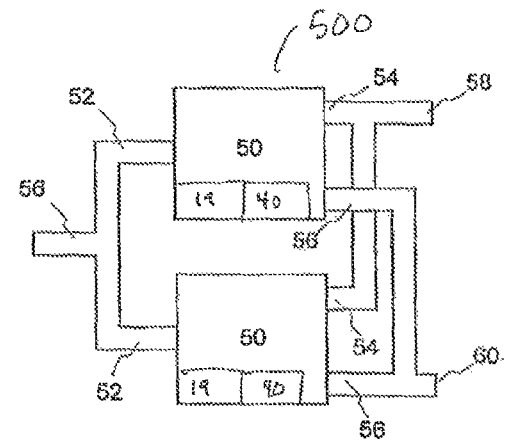
FIG. 9 shows a particle sorting system for sorting parallel streams of particles.

FIG. 9 shows a particle sorting system 500 according to an alternate embodiment of the invention, comprising a plurality of sorting module 50 operating in parallel. The individual outlet duct 54 of the sorting module 50 are forwarded to a first combined outlet 58, the individual second outlet duct 56 are forwarded to a second combined outlet 60. The parallel arrangement of sorting modules yields a system of combined sorting module 50 having an overall sorting rate of N times the sorting rate of an individual sorting module 50, where N is the number of parallel connected sorting module 50.

Figure 10:
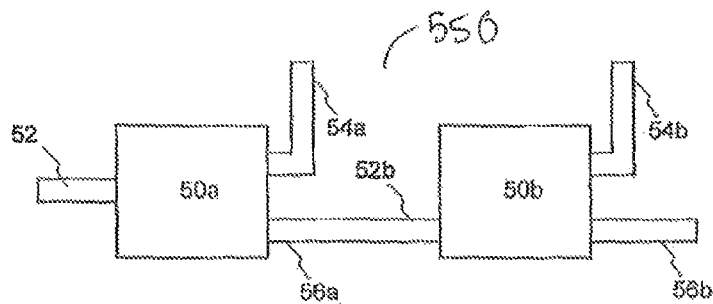
FIG. 10 shows a particle sorting system binary tree-like configuration of sorting modules.

FIG. 10 shows a particle sorting system 550 according to another embodiment, comprising a first sorting module 50a and a second sorting module 50b in series with the first sorting module 50a. The second sorting module 50b may be equipped for sorting out particles having a predetermined characteristic different than the predetermined characteristic of the particles sorted out by the first sorting module 50a. The particle stream enters the first sorting module 50a through the supply duct 52 and may contain at least two types of particles. A first type of particles is sorted out in the first sorting module 50a and leaves through the first outlet duct 54a. The remaining particles leave the first sorting module 50a through second outlet duct 56a and are fed into the second sorting module 50b via the second supply duct 52b. From this stream of particles, particles having the other predetermined characteristic are sorted out and leave through the second outlet duct 54b. Particles that posses neither of the two predetermined characteristics leave the second sorting module 50b via the second outlet duct 56b.

Figure 11:
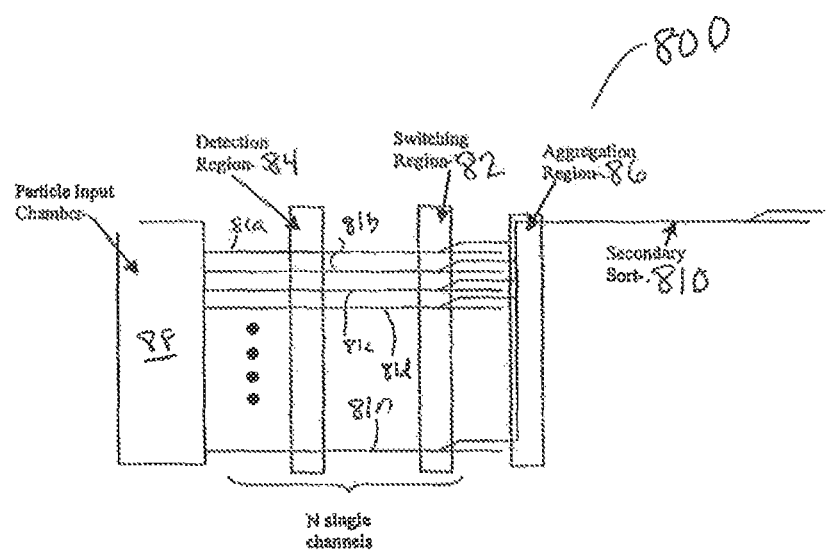
FIG. 11 illustrates a multi-stage particle sorting system for sorting parallel streams of particles in two stages.

FIG. 11 shows a hierarchical architecture for high throughput-low error sorting according to another embodiment of the invention. The embodiment shown is a two-stage particle sorting system 800 for sorting a plurality of parallel particles streams in a first stage, aggregating the outputs of the first stage and then performing a secondary sorting process on the output of the first stage. An input stream of particles in suspension 80 from a particle input chamber 88 is split among N single sorting channels 81a-81n, each channel being capable of sorting a selected number of particles per second. Each channel 81 includes a detection region 84 for examining the particles and identifying particles that have a predetermined characteristic and a switching region 82 for separating the particles having the predetermined characteristic from the other particles in the stream, as described above. The switching region 82 produces two output streams of particles: a "selected" stream and a "rejected" stream in its switching region 82 based on the measured particle characteristics at the detection region 84. The "selected" streams from each channel are aggregated in an aggregation region 86 into one stream to be sorted again in a secondary sorting channel 810. As shown, the secondary sorting channel 810 repeats the sorting process of detecting and sorting based on a predetermined characteristic.

Given that each single channel sorting process produces some error (y) rate (y is a probability less than one of a particle being "selected" by mistake) of mistaken selections, the hierarchical architecture produces an lower error rate of $y^2$ for a 2-stage hierarchy as drawn or $y^n$ for an n-stage hierarchy. For example, if the single channel error rate is 1% the 2-stage error rate is 0.01% or one part in $10^4$.

Alternatively, the architecture could have M primary sets of N sorting channels per secondary channel. Given that the application wants to capture particles that have a presence in the input at rate z and single channel sorters have a maximum sorting rate x particles per second. The system throughput is M*N*x in particles per second. The number of particles aggregated in N channels per second is N*x*z and so N*z must be less than 1 so that all particles aggregated from N channels can be sorted by a single secondary channel. To increase throughput above N=1/z one must add parallel groups of N primary+1 secondary channels. Overall throughput then comes from M*N*x with M secondary channels.

Figure 12:
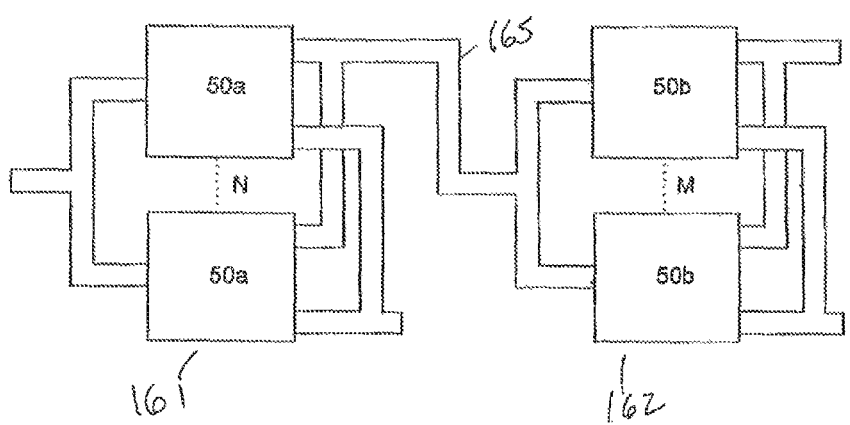
FIG. 12 illustrates a parallel particle sorting system according to an alternate embodiment of the invention.

FIG. 12 show a parallel-serial particle sorting system 160 according to another embodiment of the invention. The parallel-serial particle sorting system 160 includes a first parallel sorting module 161 and a second parallel sorting module 162. The first sorting module 161 is applied in multiple marked particles and particles having both markers are sorted out and conveyed through the exit channel 165.

Figure 13:
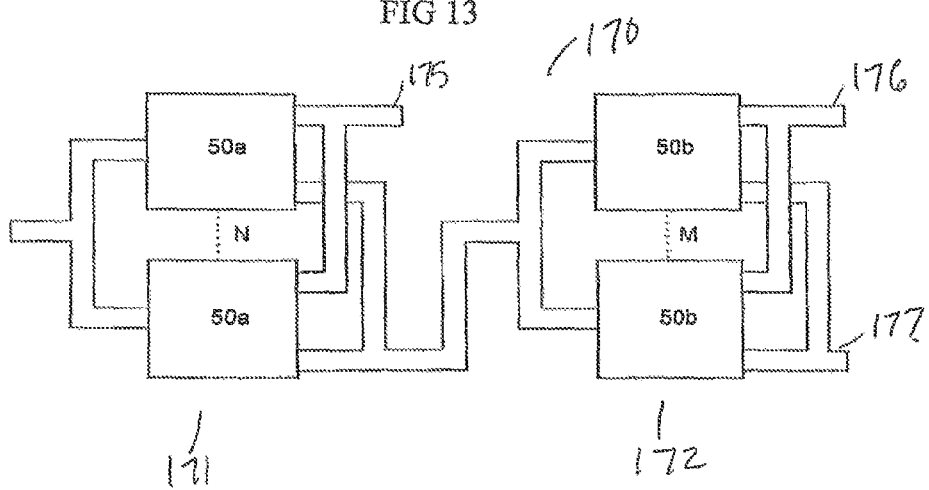
FIG. 13 illustrates a parallel particle sorting system according to another embodiment of the invention.

FIG. 13 shows another parallel-serial particle sorting system 170. The first parallel sorting module 171 separates particles having a first marker, collects the particles from the different channels and conveys the particles having the first marker through the first exit channel 175. All other particles are then fed into a second parallel sorter 172 for sorting particles having a second marker. The particles having the second marker are collected and conveyed through a second exit channel 176. Particles having neither the first marker nor the second marker are conveyed through a third exit channel 177.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A microfluidic system for sorting particles, the microfluidic system comprising:
a first microfluidic flow channel formed in a particle processing component substrate having an upstream inlet configured to introduce a fluidic stream having a plurality of particles into the first microfluidic flow channel and downstream outlets configured to output portions of the fluidic stream of particles;
a detection region located downstream of the inlet, the detection region configured to allow a particle having a predetermined characteristic to be sensed, the sensed particle being one of the plurality of particles in the fluidic stream; and
a switching device located downstream of the detection region, the switching device operatively coupled to the first microfluidic flow channel to deliver a transient pressure pulse in a direction substantially perpendicular to a flow direction of the fluidic stream of particles,
wherein the transient pressure pulse displaces and separates a selected single sensed particle from the fluidic stream of particles,
wherein the selected particle is displaced and separated from the fluidic stream of particles in a switching region,
wherein the fluidic stream of unselected particles flows into a first downstream outlet configured to output a first portion of the fluidic stream of particles,
wherein the selected particle flows into a second downstream outlet configured to output a second portion of the fluidic stream of particles,
wherein the transient pressure pulse is not generated downstream of the switching region,
wherein the switching device, when activated, does not block or partially block flow of the fluidic stream of particles, and
wherein the particle processing component substrate includes a reservoir adapted for dampening or absorbing the transient pressure pulse propagated across the microfluidic channel.

2. The microfluidic system of claim 1,
wherein the switching device is integrally provided on the particle processing component substrate, and
wherein the switching device is configured to be activated by a first external actuator.

3. The system of claim 2, further comprising a second actuator, external to and operatively associated with the first microfluidic flow channel, for processing the sample on a particle-by-particle basis.

4. The system of claim 3, wherein the first external actuator is adapted for directing particles into a first of the one or more downstream outlets and the second external actuator is adapted for directing particles into a second of the one or more downstream outlets.

5. The system of claim 1, wherein the particle processing component substrate includes a reservoir operatively associated with the switching device and adapted for originating the transient pressure pulse.

6. The microfluidic system of claim 1, wherein
the switching device introduces liquid into the microfluidic flow channel such that the transient pressure pulse is a transient hydraulic pressure pulse.

7. The system of claim 1, wherein the switching device further includes first and second side channels in fluid communication with the first microfluidic flow channel, the second side channel positioned opposite to the first side channel.

8. The system of claim 1, further including an actuator for activating the switching device and wherein the actuator is a piezoelectric actuator.

9. The system of claim 1, further including an actuator for activating the switching device and wherein the actuator is an electromagnetic actuator.

10. The system of claim 1, further including an actuator for activating the switching device and wherein the actuator is a thermopneumatic actuator.

11. The system of claim 1, further including an actuator for activating the switching device and wherein the actuator is a heat pulse generator.

12. The system of claim 1, wherein the switching device is integrally provided on the particle processing component substrate and is configured for an external actuator to operatively engage and activate the switching device.

13. The system of claim 1, wherein the switching device is configured to direct the selected particle out of the fluidic stream of particles without generating a pressure wave that travels upstream of the switching device.

14. The system of claim 1, wherein the fluidic stream of particles maintains a laminar flow when the selected particle is displaced and separated from the fluidic stream of particles.

15. A microfluidic method for producing a particle product from a sample having particles, the method comprising:
 flowing the sample as a fluidic stream of particles from an upstream inlet along a first flow path through a first microfluidic flow channel formed in a substrate of a microfluidic particle processing component;
 processing the sample on a particle-by-particle basis to produce a particle product;
 outputting a first portion of the processed sample via a first downstream outlet of the first microfluidic flow channel; and
 outputting a second portion of the processed sample via a second downstream outlet of the first microfluidic flow channel,
 wherein the step of processing includes:
  activating a switch component;
  redirecting a single selected particle out of the first flow path of the fluidic stream of particles at a switching region and into a second flow path flowing downstream into the second downstream outlet, and
  deactivating the switch component,
  wherein activating the switch component does not generate a pressure wave that travels upstream to the switching region,
  wherein activating the switch component does not shift the remainder of the fluidic stream of unselected particles from the first flow path flowing downstream into the first downstream outlet, and
 wherein activating the switch component includes using an actuator external to and operatively associated with the microfluidic particle processing component, to activate the switch component; and
 further comprising using a reservoir operatively associated with the first microfluidic flow channel to dampen or absorb a transient pressure pulse propagated across the microfluidic channel.

16. The method of claim 15, wherein the step of processing further includes using a reservoir operatively associated with the first microfluidic flow channel to originate the transient pressure pulse propagated across the first microfluidic flow channel for sorting particles on a particle-by-particle basis into the second downstream outlet.

17. The method of claim 15, wherein activating the switch component includes flexing the switch component.

18. The method of claim 15, wherein the switch component is located in a side channel and wherein the side channel is not a flow through channel.

19. A microfluidic system for sorting particles, the microfluidic system comprising:
 a first microfluidic flow channel formed in a particle processing component substrate having an upstream inlet configured to introduce a fluidic stream having a plurality of particles into the first microfluidic flow channel and downstream outlets configured to output portions of the fluidic stream of particles;
 a detection region located downstream of the inlet, the detection region configured to allow a particle having a predetermined characteristic to be sensed, the sensed particle being one of the plurality of particles in the fluidic stream;
 a switching device located downstream of the detection region, the switching device operatively coupled to the first microfluidic flow channel to deliver a transient pressure pulse in a direction substantially perpendicular to a flow direction of the fluidic stream of particles,
 wherein the transient pressure pulse displaces and separates a selected single sensed particle from the fluidic stream of particles,
 wherein the selected particle is displaced and separated from the fluidic stream of particles in a switching region,
 wherein the fluidic stream of unselected particles flows into a first downstream outlet configured to output a first portion of the fluidic stream of particles,
 wherein the selected particle flows into a second downstream outlet configured to output a second portion of the fluidic stream of particles,
 wherein the transient pressure pulse is not generated downstream of the switching region, and
 further including an actuator for activating the switching device and wherein the actuator is a piezoelectric actuator,
 wherein the particle processing component substrate includes a reservoir adapted for dampening or absorbing the transient pressure pulse propagated across the microfluidic channel.

20. The system of claim 19, wherein the particle processing component substrate includes a reservoir operatively associated with the switching device and adapted for originating the transient pressure pulse.

21. The system of claim 19, wherein the switching device further includes first and second side channels in fluid communication with the first microfluidic flow channel, the second side channel positioned opposite to the first side channel.

* * * * *